United States Patent [19]

van Andel

[11] Patent Number: Plant 5,431

[45] Date of Patent: Apr. 9, 1985

[54] ALSTROEMERIA NAMED STALRAMA

[75] Inventor: Jacob van Andel, Jac. Takkade 9a 1432 CA, Aalsmeer, Netherlands

[73] Assignee: B. V. Handelskwekerij/M. C. van Staaveren, Aalsmeer, Netherlands

[21] Appl. No.: 522,256

[22] Filed: Aug. 11, 1983

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—Charles W. Rummler

[57] ABSTRACT

A new alstroemeria cultivar having medium sized flowers in the scarlet range of red color and particularly distinguished by its abundant foliage and vigorous growth habit which produces a tall cane bearing an umbel form of inflorescence at its top with a profuse array of flowers which bloom continuously during both Spring and Fall blooming seasons.

1 Drawing Figure

BACKGROUND OF THE NEW PLANT

My new alstroemeria plant originated as a sport of "Red Sunset", U.S. Plant Pat. No. 4,635, and was discovered by me in 1979 at Aalsmeer, Holland, growing among a field of the parent variety being grown for commercial purposes at Aalsmeer. The very distinctive color of the flowers on the discovery plant and its apparent market advantage as a companion of its parent caused me to propagate this mutation at Aalsmeer by dividing the tubers from which it originated and further propagation of this plant in a similar manner through successive generations has shown that its distinctive characteristics hold true from generation to generation and appear to be firmly fixed.

DESCRIPTION OF THE DRAWING

My new alstroemeria cultivar is illustrated by the accompanying drawing which is a photographic rendition of the plant in full bloom, with certain of its flowers hand painted to show the true coloring and form of the flowers as herein specified.

DESCRIPTION OF THE NEW PLANT

The following is a detailed description of my new alstroemeria discovery with the color designations according to The R.H.S. Colour Chart published by The Royal Horticultural Society of London, England.

THE PLANT

Origin: Mutation.

Parentage: Red Sunset, U.S. Plant Pat. No. 4,635.

Classification: Alstroemeria Hybrid.

Form: A tall erect bush having a strong slender stalk topped by a simple umbel of many flowering branches.

Height: About 1.7 meters.

Growth: Vigorous, strong and upright.

Root stock: Tuberous with many buds produced successively during the year from which flower stalks grow in various stages of development during the course of the year.

*Color.*—White.

Size.—Varying in season.

Foliage:

*Quantity.*—Abundant with 30 to 40 leaves on each stem.

*Leaf size.*—Various, depending on season.

*Leaf shape.*—Elliptic.

*Texture.*—Smooth.

*Color.*—Upper side — Light Green center with Dark Green margins. Under side — Grey Green.

THE BUD

*Size: Medium.*

*Diameter.*—About 15 mm.

*Length.*—About 40 to 45 mm.

Opening rate: Slow.

Peuncle:

*Length.*—About 10 to 15 mm.

*Character.*—Extends at an angle of about 30° from the flower stem.

*Color.*—Middle Green.

Flower stem:

*Length.*—About 10 to 15 cm.

THE FLOWER

Blooming habit: Continuous and profusely during early Spring and Fall seasons.

Flower Size: Medium large.

*Diameter.*—About 6 cm.

Shape: Funnel-like.

Borne: Singly on strong umbel stems.

Petalage:

*Number of petals.*—Six.

*Arrangement.*—Two concentric rings of three petals.

*Form.*—Broad ovate.

*Texture.*—Soft.

*Aspect.*—Shiny.

*Color.*—Outer petals — 44D-48C. Reverse side — 44D and 45C/B. Inside petals — 37A and 14A. Reverse side — 37A/B and 14B.

Main stem or stalk:

*Length.*—About 1.5 meters.

*Character.*—Strong and upright.

*Color.*—Middle Green.

Persistence of bloom: Flowers hang on and dry.

Lasting quality:

*On the plant.*—15 To 20 days.

*As a cut flower.*—About 10 to 15 days.

REPRODUCTIVE ORGANS

Stamens:

*Number.*—Six.

*Arrangement.*—One opposite each petal.

*Anthers.*—Size: About 1 cm. long. Color: Greyish Yellow/Green.

*Filaments.*—Length: About 4 cm. Color: Orange/-Pink.

*Pollen.*—Color — Greyish Brown.

Pistils:

*Number.*—One.

*Style.*—Length: About 8 mm. Color: Violet/Pink.

*Stigma.*—Color — Orange.

This new variety is particularly distinguished from its parent Red Sunset by the larger size and deeper color of its flowers and by the abundance of its foliage. Its growth characteristics are about the same as those of its parent.

I claim:

1. The new and distinctive alstroemeria cultivar, substantially as herein shown and described, particularly distinguished from its parent Red Sunset (U.S. Plant Pat. 4,635) by its deeper red flower color and its abundance of foliage.

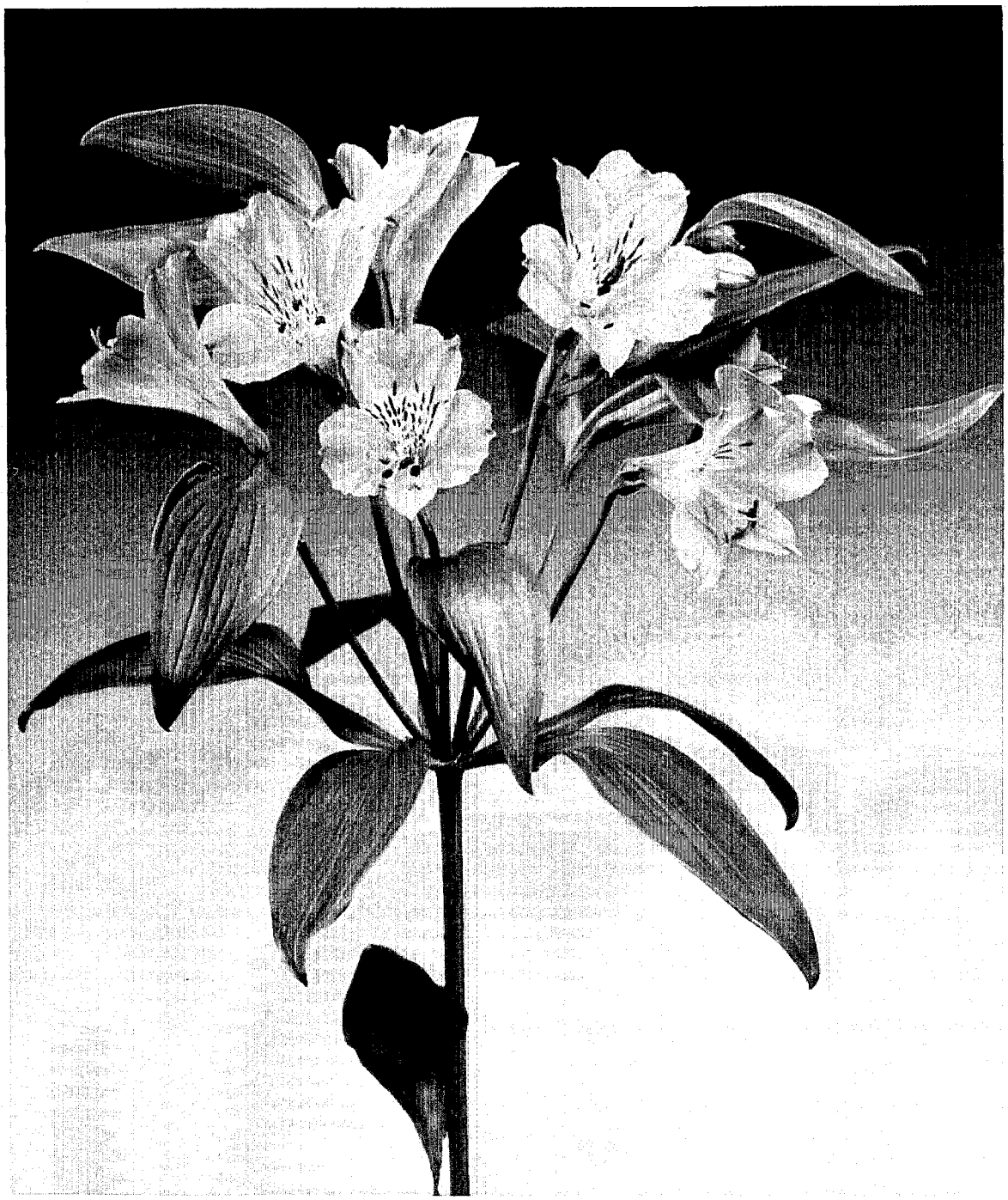

* * * * *